US012639914B2

(12) United States Patent　　　　　(10) Patent No.:　US 12,639,914 B2

Sugawara　　　　　　　　　　　　　　(45) Date of Patent:　　May 26, 2026

(54) PULSE DETECTION DEVICE AND PULSE DETECTION METHOD

(71) Applicant: Sony Interactive Entertainment Inc., Tokyo (JP)

(72) Inventor: Akihiko Sugawara, Kanagawa (JP)

(73) Assignee: Sony Interactive Entertainment Inc., Tokyo (JP)

( * ) Notice:　Subject to any disclaimer, the term of this patent is extended or adjusted under 35 U.S.C. 154(b) by 398 days.

(21) Appl. No.:　18/257,127

(22) PCT Filed:　Dec. 25, 2020

(86) PCT No.:　PCT/JP2020/048931
§ 371 (c)(1),
(2) Date:　Jun. 13, 2023

(87) PCT Pub. No.:　WO2022/137557

PCT Pub. Date: Jun. 30, 2022

(65)　　　Prior Publication Data

US 2024/0029396 A1　　Jan. 25, 2024

(51) Int. Cl.
*G06V 10/75*　　(2022.01)
*A61B 5/024*　　(2006.01)
*G06V 10/56*　　(2022.01)

(52) U.S. Cl.
CPC ........ *G06V 10/751* (2022.01); *A61B 5/02444* (2013.01); *G06V 10/56* (2022.01)

(58) Field of Classification Search
CPC .. G06V 10/758; G06V 10/56; A61B 5/02444; A61B 5/024
See application file for complete search history.

(56)　　　　References Cited

U.S. PATENT DOCUMENTS 8,666,116　B2　3/2014　Kirenko
11,445,921　B2　9/2022　Yoshizawa
(Continued)

FOREIGN PATENT DOCUMENTS

JP　　2005218507 A　　8/2005
JP　　2013506523 A　　2/2013
JP　　2016190022 A　　11/2016

OTHER PUBLICATIONS

International Search Report for corresponding PCT Application No. PCT/JP2020/048931, 4 pages, dated Mar. 9, 2021.

*Primary Examiner* — Shaghayegh Azima
(74) *Attorney, Agent, or Firm* — Kilpatrick Townsend & Stockton LLP

(57)　　　　ABSTRACT

A frame storage section stores captured images of a predetermined number of frames depicting a region including the skin of a user. A pixel value acquisition section divides the captured images into a plurality of blocks and acquires the pixel values in each block. A pixel exclusion section narrows down target pixels in each block by excluding pixels that have a green value equal to or smaller than a predetermined threshold in a case where pixel colors of each block are represented by RGB. A brightness change compensation section compensates for brightness changes by dividing the average of green values by the average of red or blue values in a case where the colors of the target pixels in each block are represented by RGB. A pulse detection section detects a pulse from temporal changes in target pixel values in each block.

20 Claims, 12 Drawing Sheets

(56) References Cited

U.S. PATENT DOCUMENTS

| | | | | |
|---|---|---|---|---|
| 2010/0067002 A1* | 3/2010 | Ishii | ....................... | A61B 5/418 |
| | | | | 356/320 |
| 2012/0195486 A1 | 8/2012 | Kirenko | | |
| 2017/0163953 A1* | 6/2017 | Wang | ................... | H04N 23/611 |
| 2017/0238842 A1* | 8/2017 | Jacquel | ................ | A61B 5/1032 |
| 2018/0042486 A1 | 2/2018 | Yoshizawa | | |
| 2020/0268281 A1* | 8/2020 | Jacquel | ................ | A61B 5/1032 |

* cited by examiner

F I G . 3

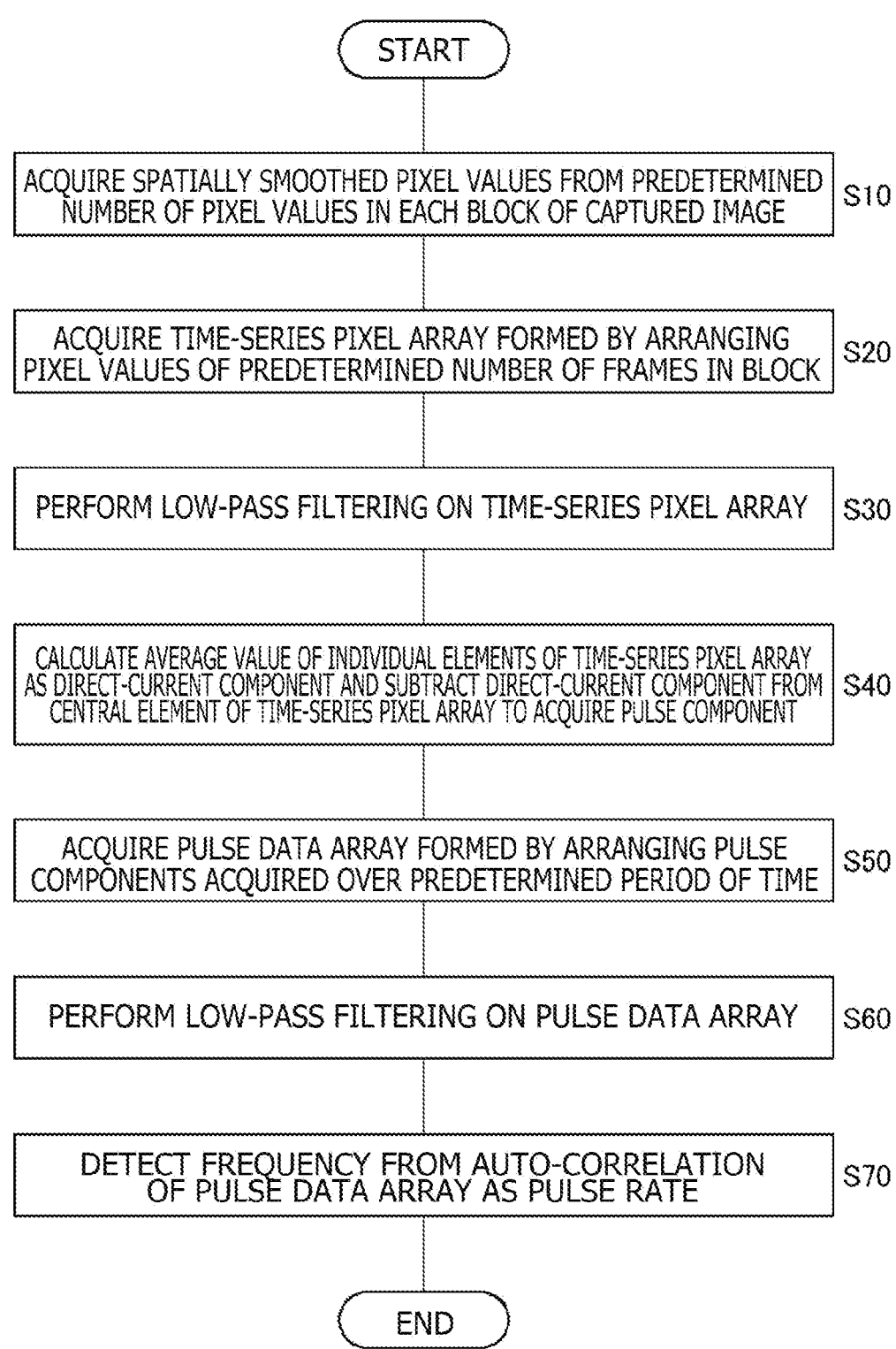

START

ACQUIRE SPATIALLY SMOOTHED PIXEL VALUES FROM PREDETERMINED NUMBER OF PIXEL VALUES IN EACH BLOCK OF CAPTURED IMAGE    S10

ACQUIRE TIME-SERIES PIXEL ARRAY FORMED BY ARRANGING PIXEL VALUES OF PREDETERMINED NUMBER OF FRAMES IN BLOCK    S20

PERFORM LOW-PASS FILTERING ON TIME-SERIES PIXEL ARRAY    S30

CALCULATE AVERAGE VALUE OF INDIVIDUAL ELEMENTS OF TIME-SERIES PIXEL ARRAY AS DIRECT-CURRENT COMPONENT AND SUBTRACT DIRECT-CURRENT COMPONENT FROM CENTRAL ELEMENT OF TIME-SERIES PIXEL ARRAY TO ACQUIRE PULSE COMPONENT    S40

ACQUIRE PULSE DATA ARRAY FORMED BY ARRANGING PULSE COMPONENTS ACQUIRED OVER PREDETERMINED PERIOD OF TIME    S50

PERFORM LOW-PASS FILTERING ON PULSE DATA ARRAY    S60

DETECT FREQUENCY FROM AUTO-CORRELATION OF PULSE DATA ARRAY AS PULSE RATE    S70

END

F I G . 4
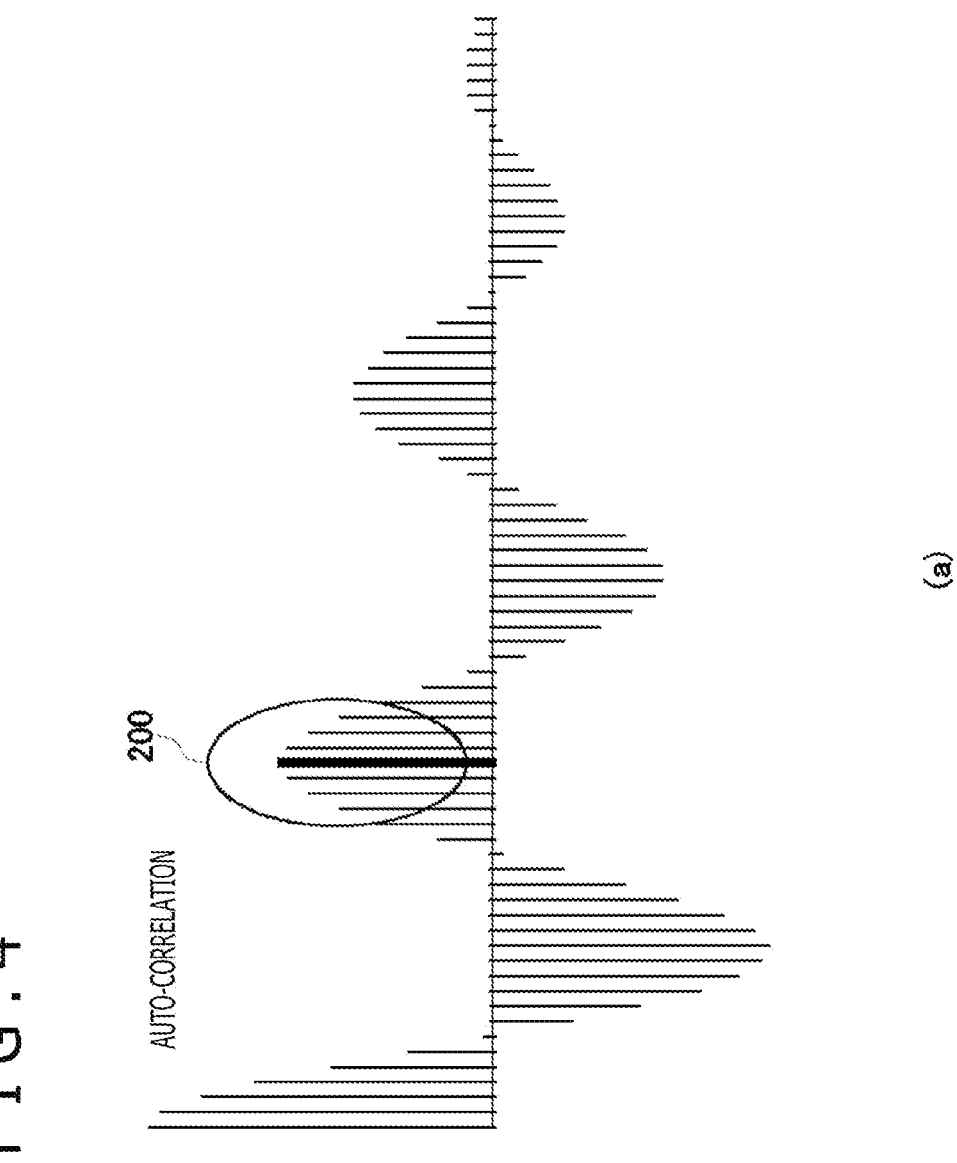

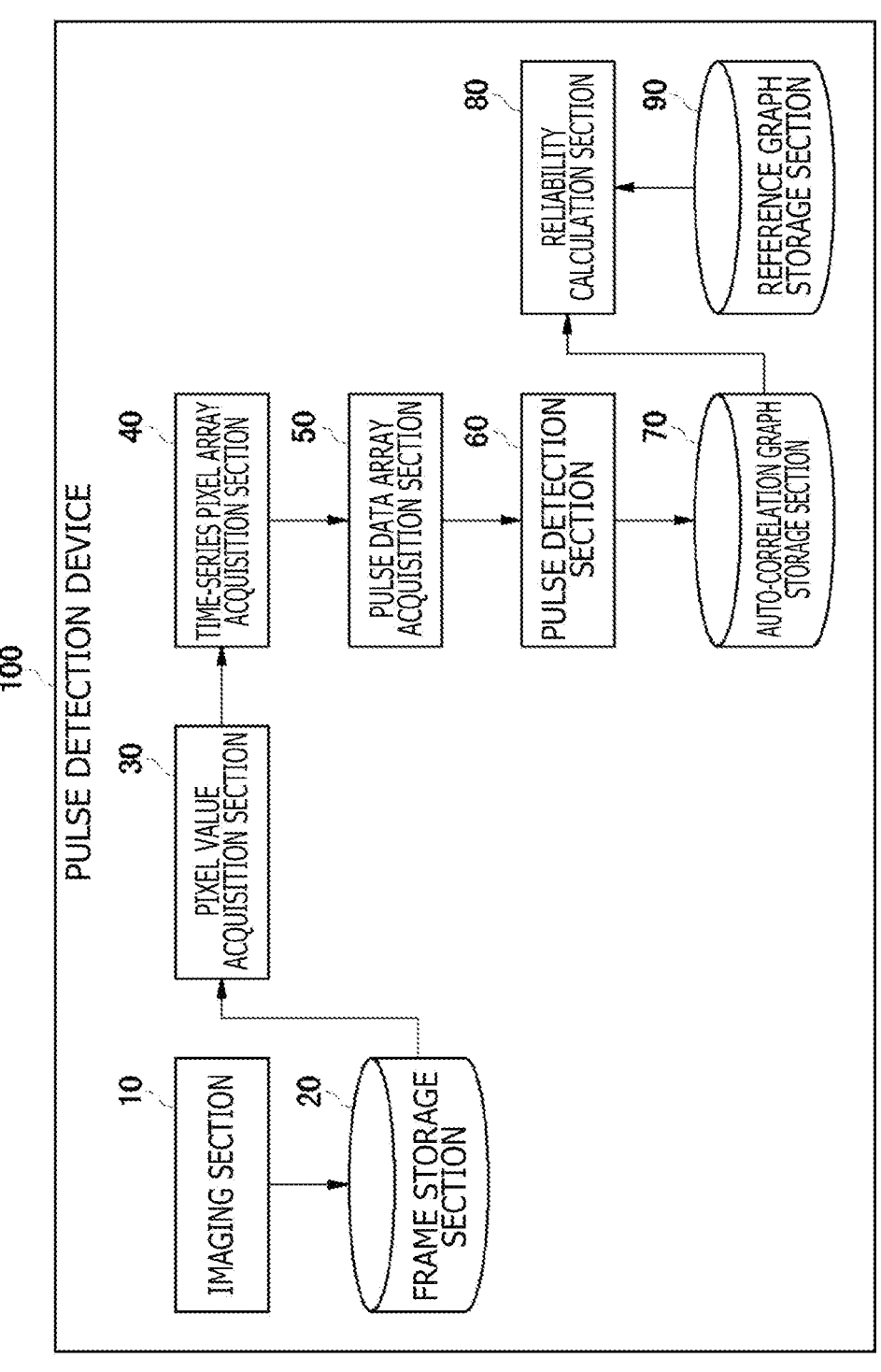
F I G . 5

F I G . 7
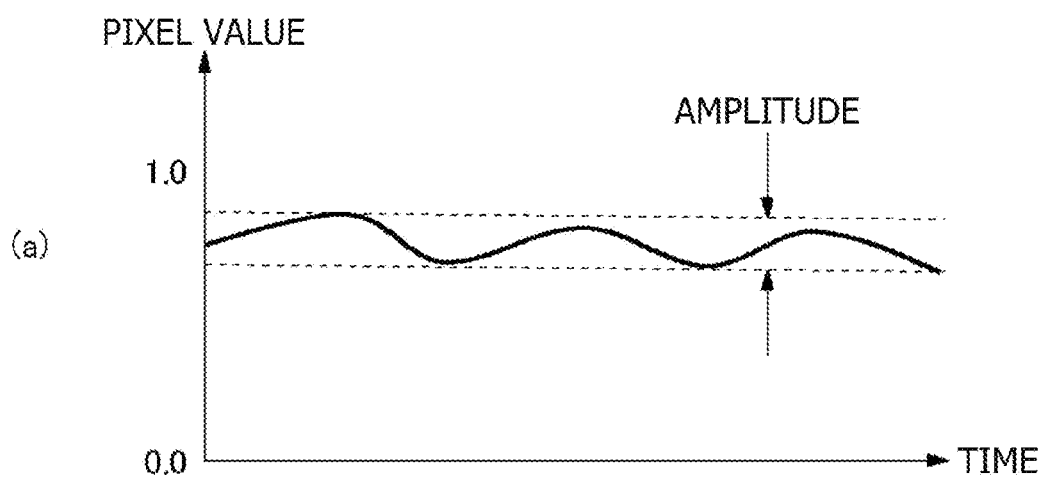
(a)
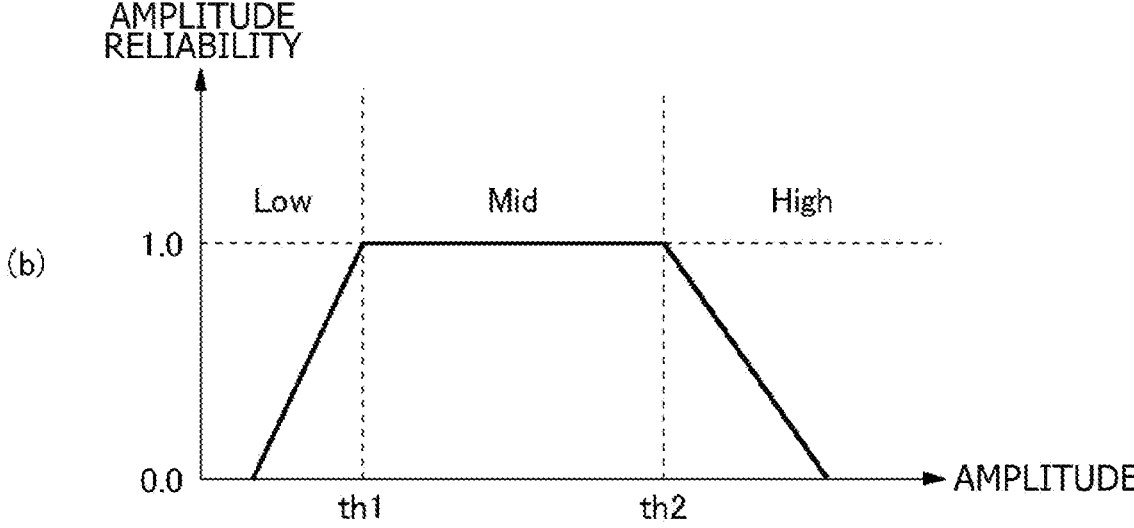
(b)

F I G . 8
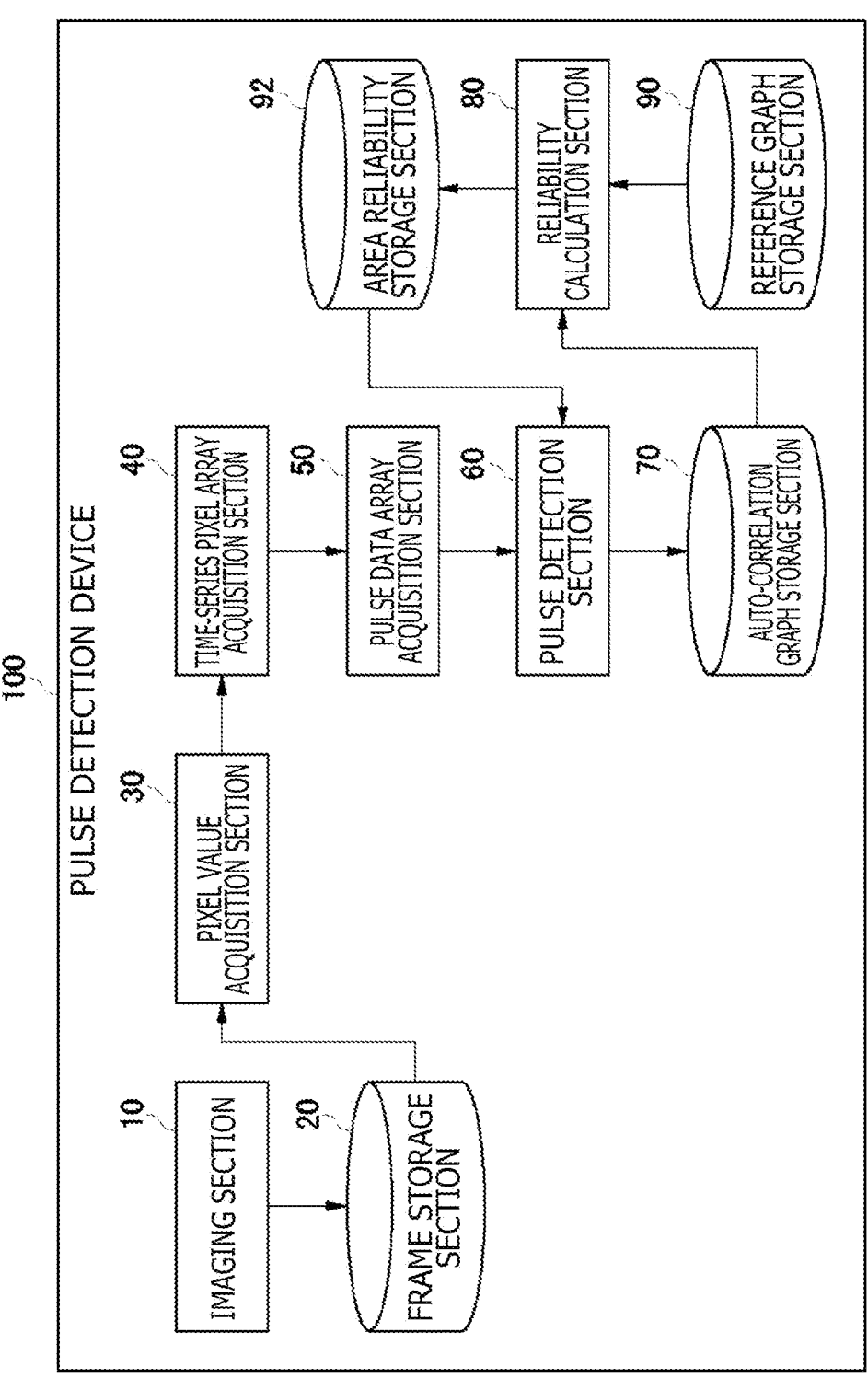

FIG.10
(a)
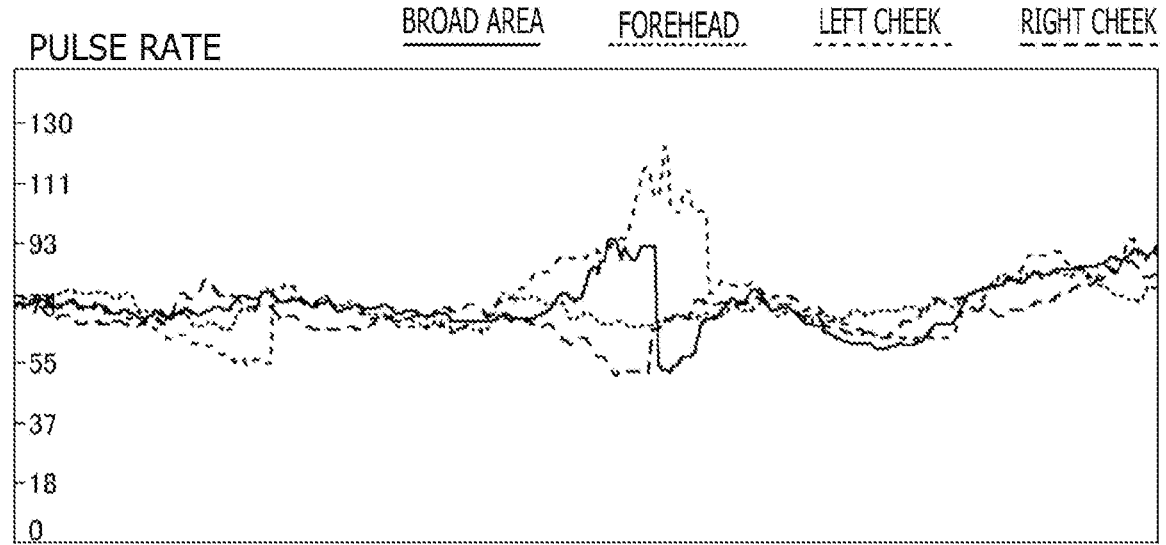
(b)
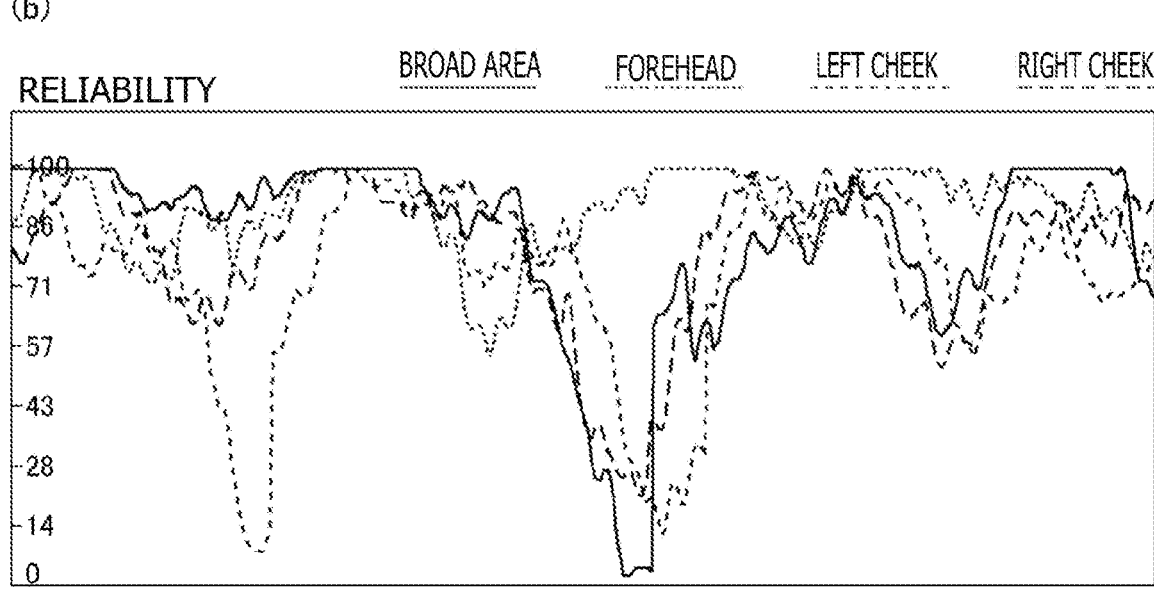

F I G . 1 1
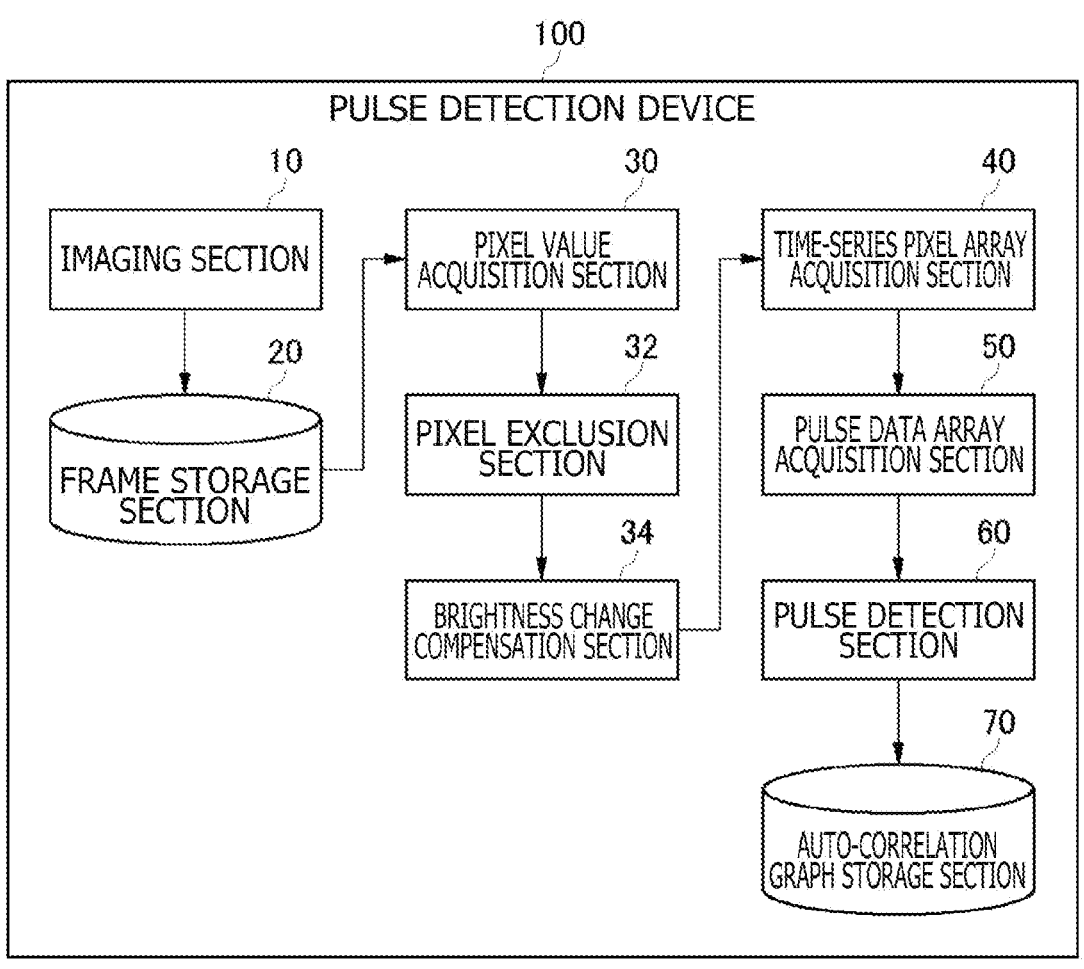

PULSE DETECTION DEVICE AND PULSE DETECTION METHOD

TECHNICAL FIELD

The present invention relates to a pulse detection technology.

BACKGROUND ART

Some home video game consoles are equipped with a camera and able to capture an image of a user playing a game, detect a facial expression of the user from captured images of the user, grasp the mental state of the user during the play of the game, and reflect the grasped mental state of the user in the progress of the game. Further, in order to detect the tension level of the user during the play of the game, a sensor for detecting a pulse is attached to the user, and a pulse measurement result outputted from the sensor is inputted to the video game consoles and reflected in the game.

Described in PTL 1 is a method for measuring vital signs from temporal changes in the density of captured images of a subject.

CITATION LIST

Patent Literature

[PTL 1] Japanese Patent Laid-open No. 2005-218507

SUMMARY

Technical Problem

There is a problem that attaching the sensor to the user to detect the pulse imposes a burden on the user. In addition, a conventional pulse detection method using captured images does not make it easy to detect slight fluctuations in the pulse. Further, the pulse is not easily measured accurately because it is affected by breathing and other body movements.

The present invention has been made in view of the above circumstances. An object of the present invention is to provide a pulse detection technology for detecting a pulse from captured images of a user with high accuracy.

Solution to Problem

In order to solve the above problem, according to an aspect of the present invention, there is provided a pulse detection device including a storage section that stores captured images of a predetermined number of frames depicting a region including the skin of a user, a pixel value acquisition section that divides the captured images into a plurality of blocks and acquires pixel values in each block, a pixel exclusion section that narrows down target pixels in each block by excluding pixels that have a green value equal to or smaller than a predetermined threshold in a case where pixel colors of each block are represented by RGB (Red, Green, Blue), and a pulse detection section that detects a pulse from temporal changes in target pixel values in each block.

According to another aspect of the present invention, there is provided a pulse detection device as well. This pulse detection device includes a storage section that stores captured images of a predetermined number of frames depicting a region including the skin of a user, a pixel value acquisition section that divides the captured images into a plurality of blocks and acquires the pixel values in each block, a brightness change compensation section that compensates for brightness changes by dividing the average of green values by the average of red or blue values in a case where the pixel colors of each block are represented by RGB, and a pulse detection section that detects a pulse from temporal changes in the pixel values in each block after brightness change compensation.

According to still another aspect of the present invention, there is provided a pulse detection method. The pulse detection method includes a pixel value acquisition step of dividing captured images of a predetermined number of frames depicting a region including the skin of a user into a plurality of blocks and acquiring pixel values in each block, a pixel exclusion step of narrowing down target pixels in each block by excluding pixels that have a green value equal to or smaller than a predetermined threshold in a case where pixel colors of each block are represented by RGB, and a pulse detection step of detecting a pulse from temporal changes in target pixel values in each block.

Any combinations of the abovementioned component elements and any conversions of expressions of the present invention between, for example, methods, devices, systems, computer programs, data structures, and recording media are also effective as the aspects of the present invention.

Advantageous Effect of Invention

The present invention is able to detect a pulse from captured images of a user with high accuracy.

BRIEF DESCRIPTION OF DRAWINGS

FIG. 3 is a flowchart illustrating a pulse wave detection procedure that is performed by the pulse detection device depicted in FIG. 1.

FIG. 4(a) illustrates an auto-correlation graph of a detected pulse wave. FIG. 4(b) is an enlarged view illustrating a peak vicinity 200 of the auto-correlation graph in FIG. 4(a).

FIG. 5 is a diagram illustrating a configuration of the pulse detection device according to a second embodiment.

FIG. 7(a) is a diagram illustrating a detected pulse wave. FIG. 7(b) is a diagram illustrating amplitude reliability.

FIG. 8 is a diagram illustrating a configuration of the pulse detection device according to a third embodiment.

FIG. 10(a) and FIG. 10(b) are diagrams respectively illustrating temporal changes in a pulse rate and temporal changes in reliability detected in each area.

FIG. 11 is a diagram illustrating a configuration of the pulse detection device according to a fourth embodiment.

DESCRIPTION OF EMBODIMENTS

First Embodiment

Figure 1:
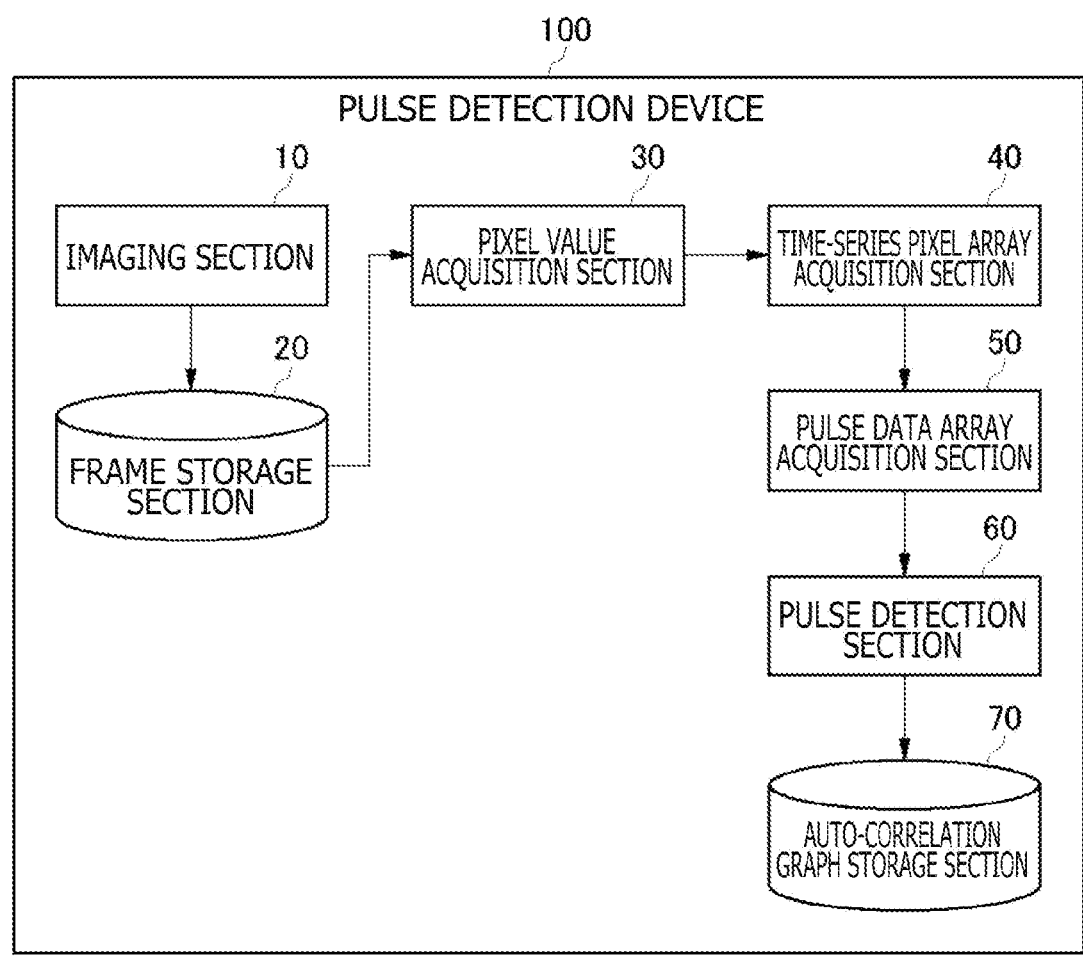
FIG. 1 is a diagram illustrating a configuration of a pulse detection device according to a first embodiment.

FIG. 1 is a diagram illustrating a configuration of a pulse detection device 100 according to a first embodiment. The pulse detection device 100 includes an imaging section 10, a frame storage section 20, a pixel value acquisition section 30, a time-series pixel array acquisition section 40, a pulse data array acquisition section 50, a pulse detection section 60, and an auto-correlation graph storage section 70.

The imaging section 10 captures images of a human body part with exposed skin such as the face of a user, and stores the captured images in the frame storage section 20. The frame storage section 20 stores the captured images of a predetermined number of frames.

The skin of the face has many capillaries, and is thus suitable for pulse imaging. In addition to the face, the palm of a hand and the sole of a foot are also suitable for capillary imaging because they are low in melanin. When pulsation occurs, the capillaries also pulsate. When images of the capillaries of skin are captured, a pulse can be detected from temporal changes in pixel values of the captured images because reflected light also changes due to capillary pulsation.

The pixel value acquisition section 30 divides the captured images stored in the frame storage section 20 into a plurality of blocks, and acquires the pixel values in each block. A region suitable for pulse wave detection is within a face region with exposed skin and shows little motion. For example, the face region of the captured images is divided into blocks, namely, the forehead, the right cheek, the left cheek, and the nose, in order to acquire the pixel values in each block. The number of pixels may vary from one block to another.

It is preferable that the pixel value acquisition section 30 acquire, as the pixel values, green values in a case where pixel colors of each block are represented by RGB.

Skin includes epidermis and dermis. The dermis is located below the epidermis. When the epidermis is transparent and thin, visible light penetrates the dermis so that an image of the capillaries can be captured. The penetrating power of visible light depends on wavelength. The longer the wavelength of visible light, the deeper the visible light penetrates into the skin. Red light has the longest wavelength and penetrates deep into the skin. However, the red light penetrates too deeply, so that images of irrelevant things other than the capillaries are captured. Blue light has the shortest wavelength, does not penetrate deep into the skin, and is thus unsuitable for capillary imaging. Green light penetrates the dermis below the epidermis, is easily absorbed by red blood cells, and is thus suitable for capillary imaging.

The pixel value acquisition section 30 acquires spatially smoothed pixel values by adding up a predetermined number of pixel values in each block. The pixel value acquisition section 30 may add up all the pixel values in a block or add up some of the pixel values in a block. In a case of 8-bit pixels, a pulse wave signal detected from one pixel is so small that there is very little change in the least significant bit. Therefore, the pulse wave signal can be amplified by adding up the pixel values in a block. Further, adding up the pixel values in a block plays the role of a spatial low-pass filter (LPF) for spatially smoothing the pixel values in a block.

The time-series pixel array acquisition section 40 acquires a time-series pixel array that is formed by arranging the pixel values of a predetermined number of frames in each block, which are acquired by the pixel value acquisition section 30. For example, in a case where the frame rate of video is 30 frames per second, the time-series pixel array acquired by the time-series pixel array acquisition section 40 is generated for each block by chronologically arranging 30 pixel values of a 1-second period, that is, the pixel values of 30 frames.

The time-series pixel array acquisition section 40 may acquire a temporarily smoothed time-series pixel array by performing low-pass filtering on the time-series pixel array. When an image sensor is used for capturing an image, values detected by the image sensor generally include noise. Performing low-passing filtering on the time-series pixel array plays the role of a temporal low-pass filter for removing time-direction noise from the values detected by a sensor.

The pulse data array acquisition section 50 calculates the average value of individual elements of the time-series pixel array as a direct-current (DC) component, extracts a central element in the time-series pixel array as an alternating-current (AC) component, and subtracts the direct-current component from the alternating-current component to acquire a pulse component. Subtracting the direct-current component from the alternating-current component of the time-series pixel array performs high-pass filtering (HPF) on the time-series pixel array.

The pulse data array acquisition section 50 proceeds with the acquisition of the pulse component of each frame, and thus acquires a pulse data array that is formed by arranging the pulse components acquired over a predetermined period of time. It is assumed that the predetermined period of time is equivalent to at least two standard pulse periods (e.g., 2.5 seconds). An instantaneous pulse can be detected by using a pulse wave signal as short as approximately two pulse periods. Using a long pulse wave signal results in pulse averaging and thus results in a failure to detect an instantaneous change in the pulse.

The pulse data array acquisition section 50 may acquire a temporarily smoothed pulse data array by performing low-pass filtering on the pulse data array. The amplitude of the pulse wave signal obtained in this case varies in the time direction depending on the method adopted for alternating-current component calculation. Performing low-pass filtering on the pulse data array plays the role of a temporal low-pass filter for eliminating the time-direction variation of the pulse wave amplitude.

In the above situation, it is preferable that low-pass filtering performed on the time-series pixel array be higher in filter strength than low-pass filtering performed on the pulse data array. The reason is that temporal noise included in raw data detected by the image sensor is relatively high and is severer than the waveform distortion of the pulse wave signal, which is caused by amplitude variation.

The pulse detection section 60 determines the auto-correlation of the pulse data array, and stores an auto-correlation graph in the auto-correlation graph storage section 70. The pulse detection section 60 detects a point at which the auto-correlation graph of the pulse wave signal is the second local maximum, acquires the time on the horizontal axis of the second local maximum point as the period of the pulse wave signal, and acquires the reciprocal of the acquired period as the frequency of the pulse wave signal. The pulse detection section 60 outputs, as the pulse rate, the frequency of the pulse wave signal that is detected by auto-correlation.

Figure 2:
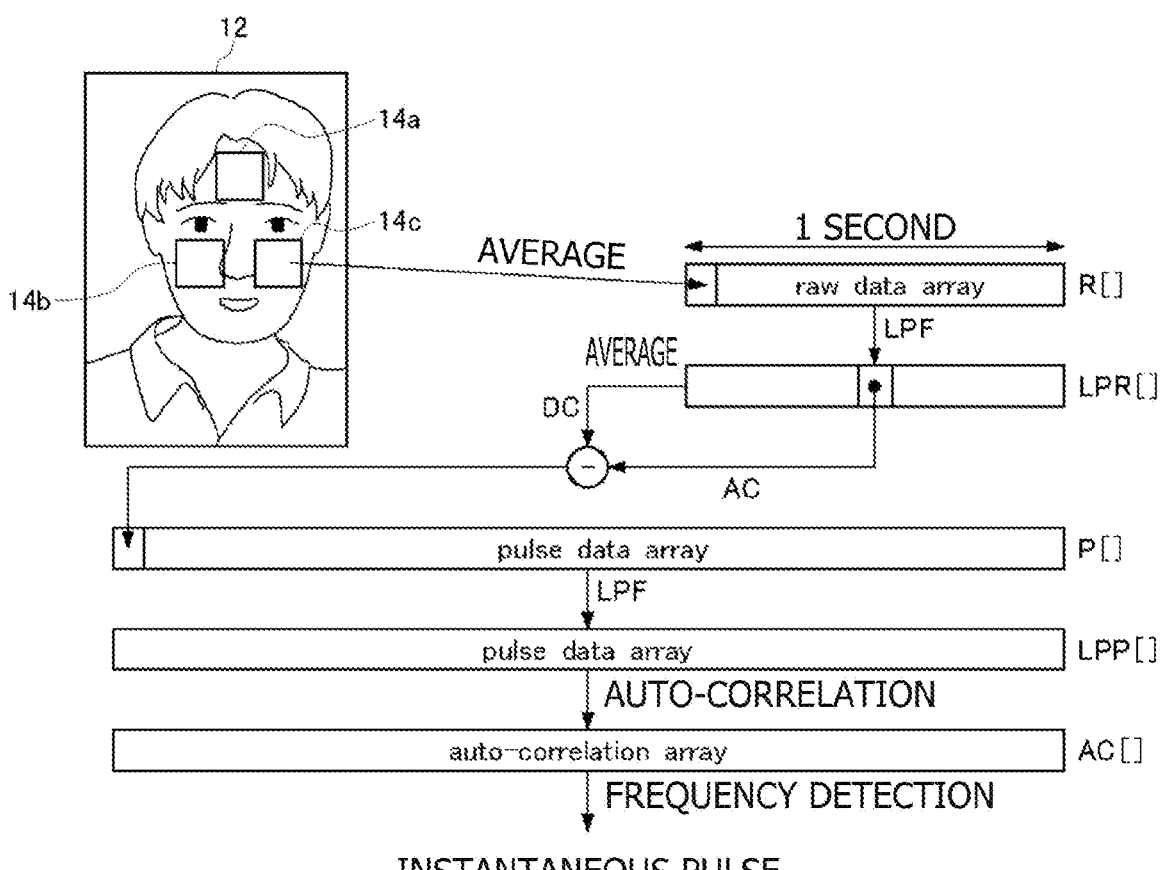
FIG. 2 is a diagram illustrating the data structure of signals that are used by the pulse detection device depicted in FIG. 1.

FIG. 2 is a diagram illustrating the data structure of signals that are used by the pulse detection device 100.

The pixel value acquisition section 30 acquires pixel values from individual blocks of a user's face image 12 captured by the imaging section 10, namely, the forehead 14a, the right cheek 14b, and the left cheek 14c, adds up the pixel values in the blocks, and stores the result of addition in a time-series pixel array R[ ], which is a raw data array. When, for example, the pixel values of 30 frames per second are stored in the array, the time-series pixel array R[ ] having 30 elements is acquired. As the frames of the captured image progress, the individual elements of the time-series pixel array R[ ] are shifted rightward, the i-th element is copied to the (i+1)-th element, and the pixel values obtained from a new frame are stored in the first element of the time-series pixel array R[ ].

The pixel value acquisition section 30 performs low-pass filtering on the time-series pixel array R[ ] at a filter strength N_raw_data. More specifically, a moving average indicated, for example, by the equation below is repeatedly performed a number of times based on the filter strength N_raw_data. For example, the filter strength N_raw_data is set to 10 in order to repeatedly perform the moving average 10 times.

$$R'[i]=0.25*R[i-1]+0.5*R[i]+0.25*R[i+1]$$

It is assumed that a time-series pixel array obtained by performing low-pass filtering on the time-series pixel array R[ ] at the filter strength N_raw_data is LPR[ ].

The pulse data array acquisition section 50 calculates the average value of the individual elements of the time-series pixel array LPR[ ] as a direct-current component, and acquires an initial pulse component P[0] by subtracting the direct-current component from a central element in the time-series pixel array LPR[ ].

Next, the pulse data array acquisition section 50 copies the pulse component P[0] to a pulse component P[1] and acquires the pulse component P[0] of the next frame. Further, the pulse data array acquisition section 50 copies the pulse component P[1] to a pulse component P[2], copies the pulse component P[0] to the pulse component P[1], and additionally acquires the pulse component P[0] of the next frame. The above sequence is repeated for a predetermined period, for example, 2.5 seconds, in order to acquire a pulse data array P[ ] that is formed by arranging the pulse components. In a case where the frame rate is 30 frames per second, the number of elements of the pulse data array P[ ] is 30*2.5=75.

As the frames of the captured image progress in the above-described manner, the individual elements of the pulse data array P[ ] are shifted rightward, the i-th element is copied to the (i+1)-th element, and the pulse component of a new frame is stored in the first element of the pulse data array P[ ].

The pulse data array acquisition section 50 performs low-pass filtering on the pulse data array P[ ] at a filter strength N_pulse_data. More specifically, a moving average indicated, for example, by the equation below is repeatedly performed a number of times based on the filter strength N_pulse_data. For example, the filter strength N_pulse_data is set to 2 in order to repeatedly perform the moving average three times.

$$P'[i]=0.25*P[i-1]+0.5*P[i]+0.25*P[i+1]$$

It is assumed that a pulse data array obtained by performing low-pass filtering on the pulse data array P[ ] at the filter strength N_pulse_data is LPP[ ].

The pulse detection section 60 uses the following equation to determine an auto-correlation AC[t] with respect to a time lag t of the pulse data array LPP[ ].

$$AC[t]=SUM(LPP[n]*LPP[n+t])$$

The pulse detection section 60 determines the auto-correlation AC[t] with respect to a range from t=0 to t=N (N is the number of elements of the pulse data array LPP[ ]), acquires, as a pulse wave period, a time T at which the auto-correlation AC[T] is the second local maximum point, and outputs, as the pulse rate, a frequency that is the reciprocal of the pulse wave period.

There is a general method for detecting the frequency of a pulse wave signal by performing fast Fourier transform on the pulse wave signal. For the fast Fourier transform, at least 512 pieces of data are required. In a case where the frame rate is 30 frames per second, over ten-second pulse wave signals are analyzed. Therefore, although the average value of over ten-second pulses is obtained, instantaneous pulses are not obtained. A pulse detection method according to the present embodiment uses auto-correlation. Therefore, when the pulse wave signals are superimposed while they are shifted from each other by one period, the auto-correlation is maximized, so that the period of the pulse wave signals can be detected. Consequently, instantaneous pulses can be obtained from the auto-correlation of pulse wave signals of a duration as short as approximately two periods. The pulse detection method according to the present embodiment is suitable for detecting slight fluctuations in the pulse.

FIG. 3 is a flowchart illustrating a pulse wave detection procedure that is performed by the pulse detection device 100.

The pixel value acquisition section 30 acquires spatially smoothed pixel values from a predetermined number of pixel values in each block of a captured image (step S10).

The time-series pixel array acquisition section 40 acquires a time-series pixel array that is formed by arranging the pixel values of a predetermined number of frames in a block (step S20). The time-series pixel array acquisition section 40 performs low-pass filtering on the time-series pixel array (step S30).

The pulse data array acquisition section 50 calculates the average value of individual elements in the time-series pixel array as a direct-current component, and acquires a pulse component by subtracting the direct-current component from a central element in the time-series pixel array (step S40). The role of a high-pass filter is played by selecting the central element as an alternating-current component and subtracting the direct-current component from the alternating-current component. The reasons why the central element is selected as the alternating-current component are that substantially the same number of elements exist before and after the central element when low-pass filtering is performed on the time-series pixel array and that low-pass filtering can be performed by substantially equally weighting before and after the time.

The pulse data array acquisition section 50 acquires a pulse data array that is formed by arranging pulse components acquired over a predetermined period of time (step S50). The pulse data array acquisition section 50 performs low-pass filtering on the pulse data array (step S60).

The pulse detection section 60 determines the period of pulse wave signals from the auto-correlation of the pulse data array, and detects, as the pulse rate, a frequency that is the reciprocal of the period of pulse wave signals (step S70).

The foregoing description assumes that the frequency is determined from the local maximum point of the auto-correlation graph depicting the detected pulse wave signals. However, the pulse detection section 60 is able to improve the accuracy of pulse rate detection by detecting, as the pulse rate, the frequency corresponding to a peak that is obtained by applying a quadratic curve to a peak vicinity of the auto-correlation of a detected pulse wave. When the frequency is detected from the local maximum point of the auto-correlation graph in a case where the frame rate of the captured image is 30 fps, the temporal resolution is $\frac{1}{30}$ seconds so that the accuracy of frequency detection is not high. Therefore, the accuracy of detection is improved by applying the quadratic curve to the peak vicinity to interpolate the auto-correlation graph, and detecting the frequency at the local maximum point of the applied quadratic curve.

FIG. 4(a) illustrates the auto-correlation graph of the detected pulse wave. FIG. 4(b) is an enlarged view illustrating the peak vicinity 200 of the auto-correlation graph in FIG. 4(a). When the temporal resolution is $\frac{1}{30}$ seconds, the position indicated by the symbol 210b is the local maximum point of the auto-correlation graph. However, when a quadratic curve 230 passing through the values 210a, 210b, and 210c of the auto-correlation graph in the peak vicinity is applied, the position at which the quadratic curve 230 is at its local maximum is given by the symbol 220. The accuracy of detection can be improved by determining the frequency of the detected pulse wave from the local maximum point 220 of the quadratic curve 230.

Second Embodiment

FIG. 5 is a diagram illustrating a configuration of the pulse detection device 100 according to a second embodiment. The pulse detection device 100 according to the second embodiment includes a reliability calculation section 80 and a reference graph storage section 90 in addition to the component elements of the pulse detection device 100 depicted in FIG. 1. Component elements and operations corresponding to those described in conjunction with the pulse detection device 100 depicted in FIG. 1 will not be redundantly described.

The reference graph storage section 90 stores, as a reference graph, the auto-correlation graph of the pulse data array that is formed by arranging noise-free pulse components acquired over a predetermined period of time. In order to model a frequent pulse wave as a reference pulse wave, the reference graph storage section 90 registers, as the reference graph, the auto-correlation graph of a noise-free reference pulse wave that is obtained when, for example, the pulse rate is stable, increasing, or decreasing.

In order to compare the auto-correlation graph of an actually detected pulse wave with the reference graph of the reference pulse wave, it is necessary that the actually detected pulse wave and the reference pulse wave match in fundamental frequency. The fundamental frequency derived from the auto-correlation graph of a detected pulse wave varies with the pulse rate. Meanwhile, the fundamental frequency in the reference graph of the reference pulse wave is fixed, for example, at 60 bpm (beats per minute). In order to evaluate waveform similarity by performing cross-correlation between the auto-correlation graph of the detected pulse wave and the reference graph of the reference pulse wave, it is necessary that the detected pulse wave and the reference pulse wave be equal in fundamental frequency. Therefore, "frequency standardization" is performed to expand or contract the data of the pulse data array of the detected pulse wave in the time-axis direction as needed to ensure that the fundamental frequency in the auto-correlation graph of the detected pulse wave is the same 60 bpm as the fundamental frequency in the reference graph of the reference pulse wave.

Figure 6:
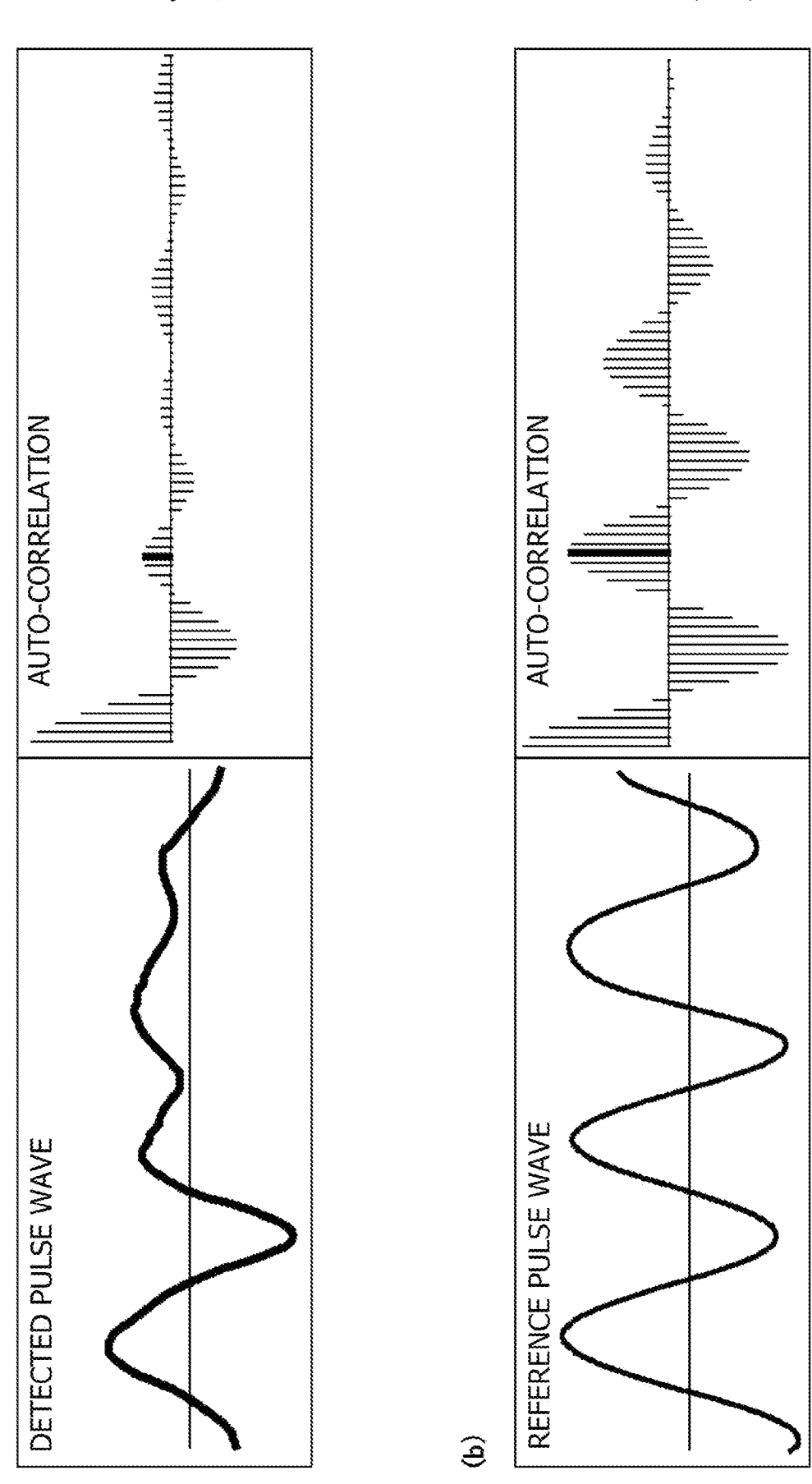
FIG. 6(a) is a diagram illustrating a detected pulse wave and an auto-correlation graph depicting the detected pulse wave.
FIG. 6(b) is a diagram illustrating a reference pulse wave and an auto-correlation graph depicting the reference pulse wave.

FIG. 6(a) depicts the detected pulse wave and its auto-correlation graph. FIG. 6(b) depicts the reference pulse wave and its auto-correlation graph. The horizontal axis value of the second local maximum point of the auto-correlation graph is a fundamental period, and the reciprocal of the fundamental period is the fundamental frequency. The frequency standardization is performed to provide correction in such a manner that the fundamental frequency of auto-correlation of the detected pulse wave matches the fundamental frequency of auto-correlation of the reference pulse wave.

The reliability calculation section 80 calculates the cross-correlation between the auto-correlation graph of the detected pulse wave, which is stored in the auto-correlation graph storage section 70, and the reference graph of the reference pulse wave, which is stored in the reference graph storage section 90, and determines waveform reliability in accordance with a cross-correlation value obtained from the calculation. The cross-correlation CC is given by the sum of products between individual elements of the auto-correlation graph AC of the detected pulse wave and individual elements of the reference graph REF of the reference pulse wave as indicated in the following equation.

$$CC=SUM(AC[n]*REF[n])$$

The waveform similarity between the auto-correlation graph of the detected pulse wave and the reference graph of the reference pulse wave increases with an increase in the cross-correlation value. The reliability calculation section 80 determines the cross-correlation value between the auto-correlation graph of the detected pulse wave and the reference graph of each reference pulse wave registered in the reference graph storage section 90, and regards the resulting maximum value as final waveform reliability. The waveform reliability is an index for determining whether the waveform of the detected pulse wave bears a likeness to a pulse wave.

Further, the reliability calculation section 80 determines amplitude reliability by comparing the amplitude of the waveform of a detected pulse wave signal with an upper limit value and a lower limit value that are predetermined.

FIG. 7(a) illustrates a detected pulse wave. The horizontal axis represents time, the vertical axis represents a green pixel value, and temporal changes in the pixel value are indicated by the graph. The amplitude of the detected pulse wave is given by the difference between the maximum and minimum values of the detected pulse wave.

FIG. 7(b) illustrates the amplitude reliability. The horizontal axis represents the amplitude of the detected pulse wave, and the vertical axis represents the amplitude reliability. In a case where the amplitude of the detected pulse wave is equal to or higher than the lower limit value th1 and is equal to lower than the upper limit value th2, the amplitude reliability is 1.0. In a case where the amplitude of the detected pulse wave is within the range of the lower limit value th1 to the upper limit value th2, the amplitude reliability is 1.0 because the amplitude bears a likeness to that of a pulse wave.

In a case where the amplitude of the detected pulse wave is lower than the lower limit value th1, the amplitude is lower than that of an expected pulse wave. Therefore, as the amplitude decreases from the lower limit value th1, the amplitude reliability is gradually lowered from 1.0. When the amplitude of the detected pulse wave is lower than the lower limit value, it is probable that a weak signal or noise is detected instead of a pulse wave.

In a case where the amplitude of the detected pulse wave is higher than the upper limit value th2, the amplitude is higher than that of the expected pulse wave. Therefore, as the amplitude increases from the upper limit value th2, the amplitude reliability is gradually lowered from 1.0. When the amplitude of the detected pulse wave is higher than the upper limit value, it is probable that noise is detected due to the movement of a user's body.

The reliability calculation section 80 calculates the final pulse wave reliability of a detected pulse rate from the waveform reliability and the amplitude reliability, and outputs the result of calculation. For example, the product of the waveform reliability and the amplitude reliability is calculated as the final pulse wave reliability of a pulse rate.

Third Embodiment

FIG. 8 is a diagram illustrating a configuration of the pulse detection device 100 according to a third embodiment. The pulse detection device 100 according to the third embodiment includes an area reliability storage section 92 in addition to the component elements of the pulse detection device 100 depicted in FIG. 5. Component elements and operations corresponding to those described in conjunction with the pulse detection device 100 depicted in FIG. 5 will not be redundantly described.

The pulse detection device 100 according to the first or second embodiment divides a captured image stored in the frame storage section 20 into a plurality of blocks, and acquires a pulse component from the pixel values in each block. However, the pulse detection device 100 according to the third embodiment divides the captured image into a plurality of areas, and acquires a pulse component from the pixel values in each area. There are, for example, narrow areas such as the forehead, the right cheek, and the left cheek, and a broad area including the eyes and the nose, and the plurality of areas can be designated with overlaps allowed. The number of pixels may vary from one area to another.

The pixel value acquisition section 30 acquires the pixel values in each area, adds up a predetermined number of pixel values in each area, and thus acquires spatially smoothed pixel values.

The time-series pixel array acquisition section 40 acquires a time-series pixel array that is formed by arranging the pixel values of a predetermined number of frames in each area, which are acquired by the pixel value acquisition section 30, and performs low-pass filtering on the acquired time-series pixel array.

The pulse data array acquisition section 50 acquires pulse components by subtracting the average value of individual elements in the time-series pixel array from a central element in the time-series pixel array in each area, generates a pulse data array formed by arranging the pulse components acquired over a predetermined period of time, and performs low-pass filtering on the generated pulse data array.

The pulse detection section 60 determines the auto-correlation of the pulse data array in each area, stores the auto-correlation graph of each area in the auto-correlation graph storage section 70, and outputs, as the pulse rate of each area, the frequency of a pulse wave signal detected from the auto-correlation graph of each area.

The reliability calculation section 80 calculates the cross-correlation between the auto-correlation graph of the detected pulse wave in each area, which is stored in the auto-correlation graph storage section 70, and the reference graph of the reference pulse wave, which is stored in the reference graph storage section 90, and determines waveform reliability in accordance with a cross-correlation value obtained from the calculation. Further, the reliability calculation section 80 determines amplitude reliability by comparing the amplitude of the waveform of a detected pulse wave signal in each area with an upper limit value and a lower limit value that are predetermined. The reliability calculation section 80 calculates final pulse wave reliability of a detected pulse rate regarding each area in accordance with the waveform reliability and the amplitude reliability, and stores pulse reliability of each area in the area reliability storage section 92.

The pulse detection section 60 may check pulses detected from each area to select a pulse that is stored in the area reliability storage section 92 and has the highest reliability, and outputs the selected pulse as a final pulse. The pulse detection section 60 may determine the final pulse by checking the pulses detected from each area to select pulses having reliability equal to or higher than a predetermined threshold, weighting the selected pulses based on reliability, and combining the resulting weighted pulses.

FIG. 9(a) to FIG. 9(d) illustrate a plurality of areas that are set in a captured image. For example, individual blocks of the user's face image 12, namely, the forehead 16a, the right cheek 16b, the left cheek 16c, and the broad area 16d including the eyes and the nose, are set as the plurality of areas. In this instance, the broad area 16d partly overlaps with the forehead 16a, the right cheek 16b, and the left cheek 16c.

Figure 9:
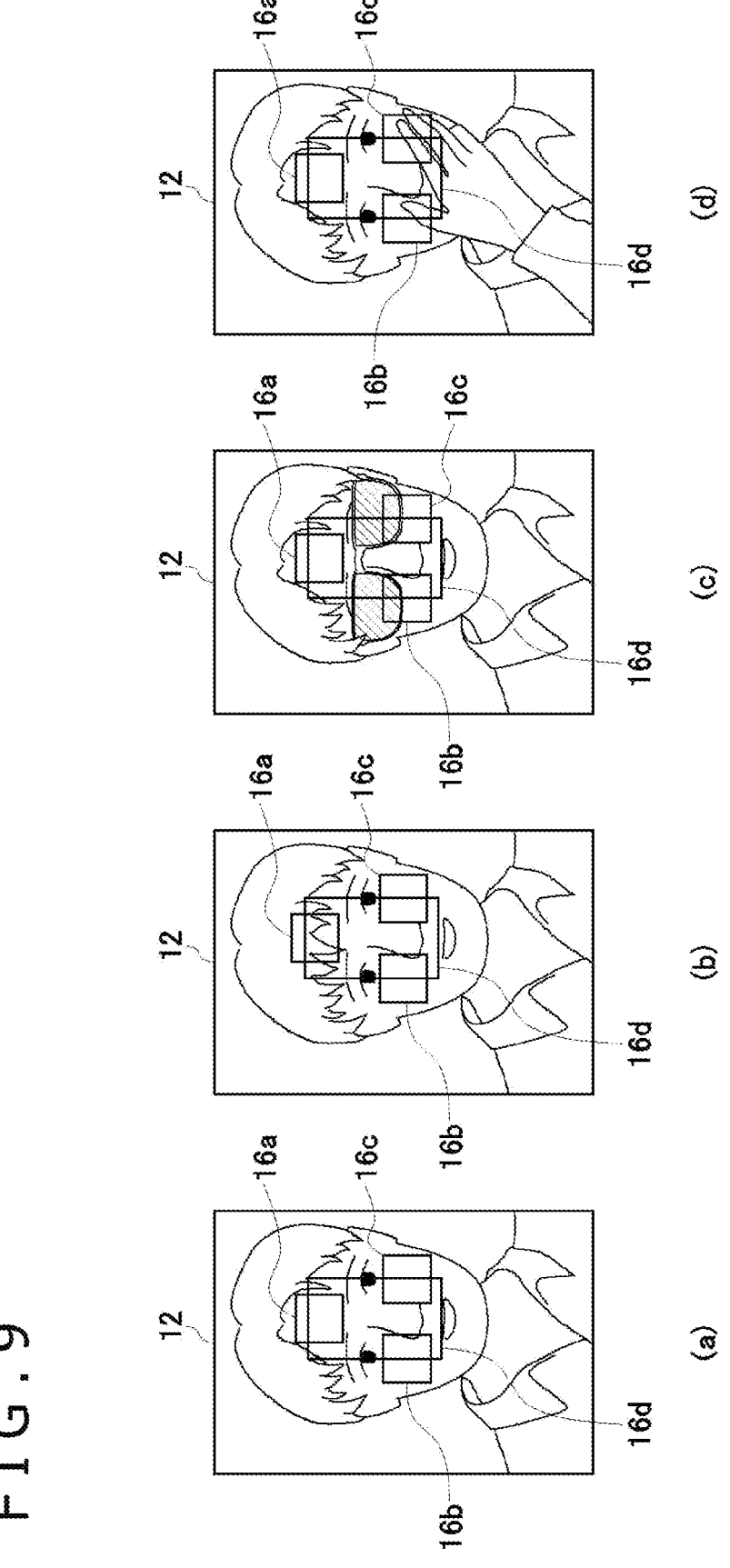
FIG. 9(a) to FIG. 9(d) are diagrams illustrating a plurality of areas that are set in a captured image.

In FIG. 9(a), the face of the user is wholly exposed. Therefore, the pulse rate is detected with high reliability in the four areas 16a to 16d.

In FIG. 9(b), the forehead is covered with hair. Therefore, the pulse rate detected from the forehead 16a has low reliability. Further, since the forehead portion of the broad area 16d is blocked by hair, it is difficult to detect the pulse components from the pixel values of the forehead portion. As a result, the detected pulse rate is lower in reliability than in a case of the broad area 16d depicted in FIG. 9(a).

In FIG. 9(c), the user wears glasses. Therefore, the right cheek 16b and the left cheek 16c are partly blocked by the glasses. As a result, the detected pulse rate is lower in reliability than in a case of the right cheek 16b and left cheek 16c depicted in FIG. 9(a). Further, it is difficult to detect the pulse components from the pixels in an area around the eyes, which is included in the broad area 16d. As a result, the detected pulse rate is lower in reliability than in a case of the broad area 16d depicted in FIG. 9(a).

In FIG. 9(d), a user's hand is placed over a mouth by the user. Therefore, the right cheek 16b, the left cheek 16c, and the broad area 16d are partly blocked by the user's hand. As a result, the detected pulse rate is lower in reliability than in a case of the right cheek 16b, left cheek 16c, and broad area 16d depicted in FIG. 9(a).

In addition to the above-mentioned cases, the pulse wave signal may be weakened or left undetected in some areas. Such situations may occur due, for instance, to a hat, head-mounted display, face mask, or other covering worn by the user, makeup or skin with dark melanin pigment, the effect of reflected light or shadow, or the movement of the user's face.

The degree of degradation in pulse rate reliability varies with the size of the region where the pulse wave signal is weakened or left undetected due, for instance, to a covering. The accuracy of pulse detection at each point of time can be kept high by comparing the pulse rate detected in each area with reliability at each point of time and adopting the pulse rate in a highly reliable area at each point of time.

FIG. 10(a) and FIG. 10(b) are diagrams respectively illustrating temporal changes in the pulse rate and temporal changes in reliability detected in each area.

FIG. 10(a) depicts a graph that indicates temporal changes in the pulse rate detected in each of the areas, namely, the forehead 16a, the right cheek 16b, the left cheek 16c, and the broad area 16d. Depending on the time zone, some portions of the areas are invisible due, for instance, to the movement of the user's face or blocked by a covering such as a user's hand. This weakens the pulse wave signal in an affected area, and thus destabilizes the detected pulse rate.

FIG. 10(b) depicts a graph that indicates temporal changes in the reliability of a pulse wave detected in each of the areas, namely, the forehead 16a, the right cheek 16b, the left cheek 16c, and the broad area 16d. As is obvious from the graph, the reliability of a specific area extremely degrades depending on the time zone. In a time zone where the reliability of the pulse wave detected in an area is lower than a predetermined threshold, the pulse rates detected from that area are not adopted. Meanwhile, in a time zone where the reliability of the pulse wave detected in an area is equal to or higher than the predetermined threshold, the pulse rates detected from that area are adopted, and then the final pulse rate is calculated by performing weighted averaging based on reliability, or the pulse rate detected from an area having the highest reliability is adopted as the final pulse rate.

Fourth Embodiment

FIG. 11 is a diagram illustrating a configuration of the pulse detection device 100 according to a fourth embodiment. The pulse detection device 100 according to the fourth embodiment includes a pixel exclusion section 32 and a brightness change compensation section 34 in addition to the component elements of the pulse detection device 100 depicted in FIG. 1. Component elements and operations corresponding to those described in conjunction with the pulse detection device 100 depicted in FIG. 1 will not be redundantly described.

The pixel value acquisition section 30 divides a captured image into a plurality of blocks, acquires the pixel values in each block, and supplies the acquired pixel values to the pixel exclusion section 32.

The pixel exclusion section 32 narrows down target pixels in each block by checking the pixel values in each block and excluding pixels unsuitable for pulse wave detection.

More specifically, the pixel exclusion section 32 narrows down the target pixels in each block by excluding pixels that have a green value equal to or smaller than a predetermined threshold in a case where pixel colors of each block are represented by RGB. In dark pixels, pulse wave signals are small and thus become noise. Therefore, the dark pixels having a green pixel value equal to or smaller than the predetermined threshold are excluded. In a case of 8-bit pixels having a maximum value of 255, for example, the pixels having a green value of 20 or smaller are excluded.

The pixel exclusion section 32 may narrow down the target pixels in each block by excluding pixels that have a red value equal to or greater than a predetermined threshold in a case where the pixel colors of each block are represented by RGB. No pulse wave signals are detected in pixels having saturated brightness. In a case of bright light reflected from the skin, red becomes saturated faster than green. Therefore, whether the brightness is saturated or not can be determined on the basis of the red value. Consequently, excessively bright pixels having a red pixel value equal to or greater than the predetermined threshold are excluded. In a case of 8-bit pixels having a maximum value of 255, for example, the pixels having a red value of 254 or greater are excluded. It should be noted that the pixels having a red value of 255 are excluded even if they have a green value of 150.

It is preferable that red pixels having saturated brightness be excluded from the target pixels because they are used for later-described brightness change compensation by the brightness change compensation section 34.

The pixel exclusion section 32 may further narrow down the target pixels in each block by excluding pixels shifted away from a predetermined threshold out of the color of the skin in a case where the pixel colors of each block are represented by a hue. In a case where the hue is 0.0 at the red end and 1.0 at the purple end, the pixels having a hue ranging, for example, from 0.3 to 0.85 are excluded.

The pixel exclusion section 32 supplies the target pixels in each block, which are narrowed down as described above, to the brightness change compensation section 34.

Brightness changes occur due to shadow changes caused by the movement of the user's face and illumination changes applied to the user's face. This makes it difficult to detect a pulse wave. Therefore, it is necessary to compensate for brightness changes. On the same skin, there is a positive correlation between green color changes and red and blue color changes. Consequently, the brightness is kept constant by compensating for the green pixel value having a strong pulse wave signal by using the red or blue pixel value having a weak pulse wave signal.

The brightness change compensation section 34 compensates for brightness changes by dividing the average of green values by the average of red or blue values in a case where the colors of the target pixels in each block are represented by RGB.

The brightness change compensation section 34 may compensate for brightness changes by dividing the average of green values by the sum of the average of red values and the average of blue values in a case where the colors of the target pixels in each block are represented by RGB.

The brightness change compensation section 34 supplies the green values of the target pixels, which have received the above-described brightness change compensation, to the time-series pixel array acquisition section 40.

The above description assumes that the brightness change compensation section 34 compensates for brightness changes after pixel exclusion is performed by the pixel exclusion section 32. Alternatively, however, the target pixels narrowed down by allowing the pixel exclusion section 32 to perform pixel exclusion may be supplied to the time-series pixel array acquisition section 40 without causing the brightness change compensation section 34 to compensate for brightness changes. Another alternative is to subject the pixel values in each block, which are supplied from the pixel value acquisition section 30, to brightness change compensation by the brightness change compensation section 34, and supply the resulting pixel values to the time-series pixel array acquisition section 40 without allowing the pixel exclusion section 32 to perform pixel exclusion.

Figure 12:
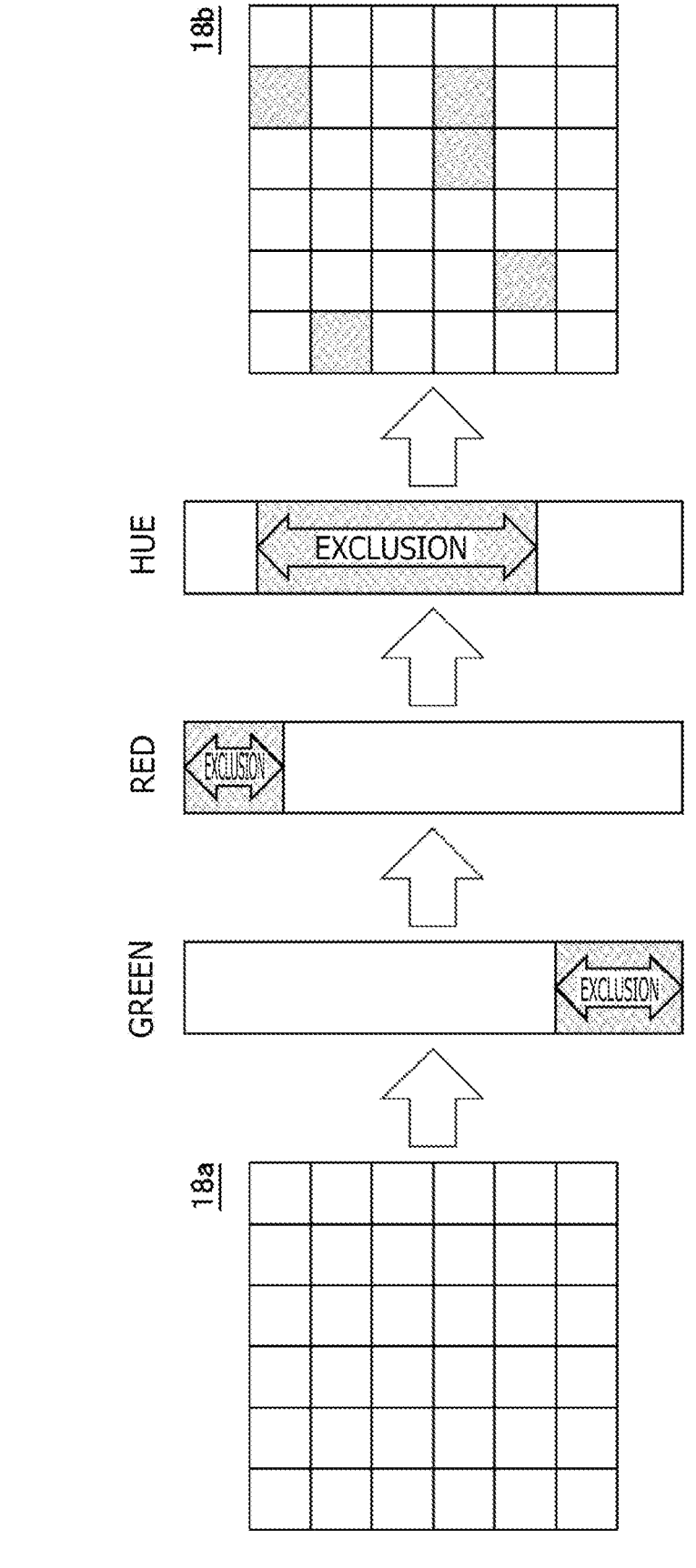
FIG. 12 is a diagram illustrating how pixels are excluded by a pixel exclusion section depicted in FIG. 11.

FIG. 12 is a diagram illustrating how the pixels are excluded by the pixel exclusion section 32 depicted in FIG. 11. The pixel exclusion section 32 excludes the pixels in a block 18a that have a green value equal to or smaller than a predetermined threshold. Next, the pixel exclusion section 32 excludes the pixels in the block 18*a* that have a red value equal to or greater than a predetermined threshold. Finally, the pixel exclusion section 32 converts the color space of pixels in the block 18*a* from RGB to, for example, HSV having three components, namely, a hue, a saturation, and a value, and excludes pixels outside a predetermined possible hue range of a skin color. As a result, the target pixels are narrowed down as indicated in a block 18*b*. Here, the excluded pixels are hatched.

As described above, the pulse detection device 100 according to the present embodiment is able to accurately measure slight fluctuations in the pulse by determining the auto-correlation of the pulse wave signal.

The present invention has been described on the basis of the embodiments. It is to be understood by persons skilled in the art that the embodiments are illustrative, that a combination of the component elements and processes described in conjunction with the embodiments may be variously modified, and further that such modifications may be made without departing from the spirit and scope of the present invention.

INDUSTRIAL APPLICABILITY

The present invention is applicable to the pulse detection technology.

REFERENCE SIGNS LIST

10: Imaging section
20: Frame storage section
30: Pixel value acquisition section
32: Pixel exclusion section
34: Brightness change compensation section
40: Time-series pixel array acquisition section
50: Pulse data array acquisition section
60: Pulse detection section
70: Auto-correlation graph storage section
80: Reliability calculation section
90: Reference graph storage section
92: Area reliability storage section
100: Pulse detection device

The invention claimed is:

1. A pulse detection device comprising:
a storage section that stores captured images of a predetermined number of frames depicting a region including skin of a user;
a pixel value acquisition section that divides the captured images into a plurality of blocks and acquires pixel values in each block;
a pixel exclusion section that narrows down target pixels in each block by excluding pixels that have a green value equal to or smaller than a first predetermined threshold and pixels that have a red value equal to or greater than a second predetermined threshold in a case where pixel colors of each block are represented by RGB, wherein the second predetermined threshold is greater than the first predetermined threshold; and
a pulse detection section that detects a pulse from temporal changes in target pixel values in each block.

2. The pulse detection device according to claim 1, wherein, when the pixel colors of each block are represented by a hue, the pixel exclusion section narrows down the target pixels in each block by further excluding pixels having a hue within a predetermined range.

3. The pulse detection device according to claim 1, further comprising:

a brightness change compensation section that compensates for brightness changes by dividing an average of green values by an average of red or blue values in a case where the colors of the target pixels in each block are represented by RGB, wherein the pulse detection section detects a pulse from temporal changes in the pixel values in each block after brightness change compensation.

4. The pulse detection device according to claim 3, wherein the brightness change compensation section compensates for brightness changes by dividing the average of green values by a sum of the average of red values and the average of blue values in the case where the pixel colors of each block are represented by RGB.

5. A pulse detection device comprising:
a storage section that stores captured images of a predetermined number of frames depicting a region including skin of a user;
a pixel value acquisition section that divides the captured images into a plurality of blocks and acquires pixel values in each block;
a brightness change compensation section that compensates for brightness changes by dividing an average of green values by a sum of an average of red values and an average of blue values in a case where the pixel colors of each block are represented by RGB; and
a pulse detection section that detects a pulse from temporal changes in the pixel values in each block after brightness change compensation.

6. A pulse detection method comprising:
dividing captured images of a predetermined number of frames depicting a region including skin of a user into a plurality of blocks and acquiring pixel values in each block;
narrowing down target pixels in each block by excluding pixels that have a green value equal to or smaller than a first predetermined threshold and pixels that have a red value equal to or greater than a second predetermined threshold in a case where pixel colors of each block are represented by RGB, wherein the second predetermined threshold is greater than the first predetermined threshold; and
detecting a pulse from temporal changes in target pixel values in each block.

7. A non-transitory, computer-readable storage medium containing a computer program, which when executed by a computer, causes the computer to implement a pulse detection method by carrying out actions, comprising:
dividing captured images of a predetermined number of frames depicting a region including skin of a user into a plurality of blocks and acquiring pixel values in each block;
narrowing down target pixels in each block by excluding pixels that have a green value equal to or smaller than a first predetermined threshold and pixels that have a red value equal to or greater than a second predetermined threshold in a case where pixel colors of each block are represented by RGB, wherein the second predetermined threshold is greater than the first predetermined threshold; and
detecting a pulse from temporal changes in target pixel values in each block.

8. The pulse detection device of claim 1, further comprising:
a time-series pixel array acquisition section configured to acquire a time-series pixel array comprising the pixel values in each block.

9. The pulse detection device of claim 8, wherein the time-series pixel array acquisition section is configured to perform low-pass filtering on the time-series pixel array to acquire a temporarily smoothed time-series pixel array.

10. The pulse detection device of claim 8, further comprising:
    a pulse data array acquisition section configured to perform high-pass filtering (HPF) on the time-series pixel array.

11. The pulse detection method of claim 6, further comprising:
    wherein, when the pixel colors of each block are represented by a hue, narrowing down the target pixels in each block by further excluding pixels having a hue within a predetermined range.

12. The pulse detection method of claim 6, further comprising:
    compensating for brightness changes by dividing an average of green values by an average of red or blue values in a case where the colors of the target pixels in each block are represented by RGB; and
    detecting a pulse from temporal changes in the pixel values in each block after brightness change compensation.

13. The pulse detection method of claim 12, further comprising:
    compensating for brightness changes by dividing the average of green values by a sum of the average of red values and the average of blue values in the case where the pixel colors of each block are represented by RGB.

14. The pulse detection method of claim 6, further comprising:
    acquiring a time-series pixel array comprising the pixel values in each block.

15. The pulse detection method of claim 14, further comprising:
    performing low-pass filtering on the time-series pixel array to acquire a temporarily smoothed time-series pixel array.

16. The pulse detection method of claim 14, further comprising:
    performing high-pass filtering (HPF) on the time-series pixel array.

17. The non-transitory, computer-readable storage medium of claim 7, wherein the actions further comprise:
    when the pixel colors of each block are represented by a hue, narrowing down the target pixels in each block by further excluding pixels having a hue within a predetermined range.

18. The non-transitory, computer-readable storage medium of claim 7, wherein the actions further comprise:
    compensating for brightness changes by dividing an average of green values by an average of red or blue values in a case where the colors of the target pixels in each block are represented by RGB; and
    detecting a pulse from temporal changes in the pixel values in each block after brightness change compensation.

19. The non-transitory, computer-readable storage medium of claim 18, wherein compensating for the brightness changes comprises dividing the average of green values by a sum of the average of red values and the average of blue values in the case where the pixel colors of each block are represented by RGB.

20. The non-transitory, computer-readable storage medium of claim 7, wherein the actions further comprise:
    acquiring a time-series pixel array comprising the pixel values in each block.

* * * * *